US010399264B2

(12) United States Patent
Huang et al.

(10) Patent No.: US 10,399,264 B2
(45) Date of Patent: Sep. 3, 2019

(54) EXTERNAL SENSOR KIT FOR INJECTION MOLDING APPARATUS AND METHODS OF USE

(71) Applicant: IMFLUX INC., Hamilton, OH (US)

(72) Inventors: Chow-Chi Huang, West Chester, OH (US); Rick Alan Pollard, Moscow, OH (US); Gene Michael Altonen, Hamilton, OH (US)

(73) Assignee: IMFLUX, INC., Hamilton, OH (US)

( * ) Notice: Subject to any disclaimer, the term of this patent is extended or adjusted under 35 U.S.C. 154(b) by 312 days.

(21) Appl. No.: 15/448,992

(22) Filed: Mar. 3, 2017

(65) Prior Publication Data
US 2017/0252956 A1    Sep. 7, 2017

Related U.S. Application Data

(60) Provisional application No. 62/303,654, filed on Mar. 4, 2016.

(51) Int. Cl.
*G01N 3/30*     (2006.01)
*B29C 45/76*    (2006.01)
(Continued)

(52) U.S. Cl.
CPC .............. *B29C 45/76* (2013.01); *B29C 45/77* (2013.01); *G01B 5/30* (2013.01); *G01L 5/0061* (2013.01);
(Continued)

(58) Field of Classification Search
CPC ................... B29C 45/76; B29C 45/77; B29C 2945/76006; B29C 2945/7626;
(Continued)

(56) References Cited

U.S. PATENT DOCUMENTS

2004/0247724 A1* 12/2004 Manner ................... B29C 45/17
425/149
2006/0082010 A1   4/2006 Saggese et al.
(Continued)

FOREIGN PATENT DOCUMENTS

JP            H044117 A      1/1992

OTHER PUBLICATIONS

International Application No. PCT/US17/20633, International Search Report and Written Opinion, dated Jun. 6, 2017.

*Primary Examiner* — Max H Noori
(74) *Attorney, Agent, or Firm* — Marshall, Gerstein & Borun LLP

(57) ABSTRACT

Embodiments within the scope of the present disclosure are directed to external sensor kits that may be included in new injection molds or retrofitted into existing injection molds in order to approximate conditions within a mold, such as pressure or the location of a melt flow front. Such kits are designed to amplify meaningful measurements obtained by the external sensor kit so that noise measurements do not prevent the approximation of conditions within a mold. In some embodiments within the scope of the present disclosure, an external sensor kit includes a strain gauge sensor, a coupon, a support bracket, and a hammer. The strain gauge sensor is placed on a surface of the coupon and measures the strain in the coupon.

9 Claims, 7 Drawing Sheets

(51) Int. Cl.
    *G01B 5/30*     (2006.01)
    *B29C 45/77*     (2006.01)
    *G01L 5/00*     (2006.01)
    *B29K 101/12*     (2006.01)

(52) U.S. Cl.
    CPC ...... *G01N 3/30* (2013.01); *B29C 2945/76006* (2013.01); *B29C 2945/7626* (2013.01); *B29C 2945/76381* (2013.01); *B29C 2945/76481* (2013.01); *B29C 2945/76545* (2013.01); *B29C 2945/76933* (2013.01); *B29K 2101/12* (2013.01)

(58) Field of Classification Search
    CPC ........... B29C 2945/76481; B29C 2945/76545; B29C 2945/76933; G01B 5/30; G01L 5/0061; G01N 3/30; B29K 2101/12

USPC ........................................................ 73/795
    See application file for complete search history.

(56) References Cited

U.S. PATENT DOCUMENTS

| | | | |
|---|---|---|---|
| 2007/0231423 A1* | 10/2007 | Han | B29C 33/06 425/549 |
| 2009/0117220 A1 | 5/2009 | Bazzo et al. | |
| 2012/0217668 A1 | 8/2012 | Catoen et al. | |
| 2013/0249357 A1* | 9/2013 | Luo | C08K 5/372 312/223.1 |
| 2014/0081208 A1* | 3/2014 | Maloney | A61M 5/486 604/121 |
| 2018/0001530 A1* | 1/2018 | Lawless, III | B29C 45/76 |
| 2018/0050475 A1* | 2/2018 | Kara | B29C 45/531 |

\* cited by examiner

EXTERNAL SENSOR KIT FOR INJECTION MOLDING APPARATUS AND METHODS OF USE

CROSS REFERENCE TO RELATED APPLICATIONS

This application is a non-provisional, and claims the benefit of the filing date of, U.S. Provisional Patent Application No. 62/303,654, filed Mar. 4, 2016, entitled "External Sensor Kit for Injection Molding Apparatus and Methods of Use." The entire contents of U.S. Provisional Application No. 62/303,654 is hereby incorporated by reference.

FIELD OF THE DISCLOSURE

This application relates generally to injection molding and, more specifically, to an external sensor kit configured to be used in an injection molding process to amplify and sense a condition, such as strain, experienced by the external sensor kit over the course of the injection molding process, the sensed condition then usable to approximate other conditions, such as pressure or melt flow front position, within an injection mold cavity for purposes of determining whether adjustments should be made to the injection molding process.

BACKGROUND

During injection molding, molten thermoplastic material flows into a mold cavity of a mold via one or more gates. The pressure within the mold cavity is an important vector, as insufficient pressure may result in improperly formed parts while excessive pressure may result in damage to the mold. The pressure at the melt flow front provides information relevant to the injection molding process overall by, for example, enabling calculation of how fast a mold cavity is filling and how long cooling of the molded part within the cavity is likely to take. Some injection molding processes aim to have the melt flow front follow a particular pressure pattern over time in order to optimize the injection molding process. For example, some injection molding processes maintain a pressure balance between the air pressure in the cavity, which changes based on the mold cavity geometry as the molten thermoplastic material moves into the cavity of the mold, and the pressure at the melt flow front, in order to produce a final product that is fully relieved of internal stresses that would otherwise undesirably lead to shrink, sink and warpage. For such injection molding systems, determining the real-time pressure at the melt flow front is important in order to determine whether the desired pressure/time curve is properly being followed and, if deviations from the pressure/time curve are identified, to make adjustments to correct the pressure of the melt flow front.

One particular motivation to monitor flow front position and/or control internal pressure at certain times during the short duration of filling of a mold cavity is to account for flow filling challenges. The term "flow filling challenge" is defined as a region of a part of a mold that forms a feature of a part to be molded which is particularly susceptible to any one or more of a number of problems that complicate the molding of the part or render the molded part more likely to suffer from one or more defects or reduced mechanical properties, such as short-fills, warp, sinks, brittleness, flash, voids, non-fills, weakness (e.g., low tensile, torsional, and/or hoop strength), high stress concentrations, low modulus, reduced resistance to chemical exposure, premature fatigue, non-uniform shrinkage, and discontinuities in color, surface texture, opacity, translucency, or transparency. Non-exhaustive examples of flow filling challenges are: Locations in a mold used to form ribs, bosses, or corners, as well as obstacles in a mold (such as core pins), and transitions (such as a change in thickness of a part to be molded, which may be a sudden stepped change in thickness or a gradual change in thickness, such as a tapered region). These can involve a transition from a relatively thick region to a relatively thin region, and then back to a relatively thick region, and may involve one or more changes in thickness. The portion of a mold cavity used to form a living hinge, which is typically an integral, relatively thin region of a molded part that permits one portion of the part, such as a flip-top of a cap, to rotate with respect to the rest of the part, poses a flow filling challenge. As the term flow filling challenge is used herein, it is contemplated that the region of the part affected by a particular challenge may be at a particular position of a mold cavity, along a region of a mold cavity, or downstream of a particular position or region of a mold cavity, and as such, a flow filling challenge need not be limited to a particular location of a change in shape of a mold cavity, but may extend beyond, i.e. downstream of, such a location.

Ideally, sensors for measuring the pressure within a mold cavity and at a melt flow front would be indirect, easy to install, and inexpensive. Direct sensors, such as sensors placed within a mold cavity, leave undesirable marks on part surfaces. For example, while demand for injection molded parts with high gloss finishes has been increasing, direct sensors positioned in the mold cavity have a tendency to mar the high gloss finish of the parts. As a result, indirect sensors that are not located in the mold cavity are preferable. Some current indirect sensors include parting line sensors, ejector or static pin sensors, and ultrasonic sensors. Unfortunately, these indirect sensors cannot always be placed in optimal locations, sometimes require that a mold apparatus undergo a period of downtime in order to be machined so that the sensor can be mounted, and can be expensive. Strain gauge sensors have been used in the past in conjunction with molding apparatuses having ejector sleeves or long core pins, but not all injection molding apparatuses are configured to include an ejector sleeve or long core pin.

More recently, external sensors, such as strain gauges, have been placed on a mold surface in order to measure how a condition, such as strain, changes over the course of a standard injection molding process. In a typical injection molding apparatus, a mold cavity is formed between two mold sides, which are held together under pressure by a press or clamping unit. Thus, along the parting line of the mold, a closing force is exerted by the press or clamping unit. When molten thermoplastic material is injected into the mold cavity, the molten thermoplastic material exerts an opening force along the parting line of the mold. Ideally, the opening force exerted by the molten thermoplastic material is less than the closing force exerted by the clamping unit. If the opening force is greater than the closing force, the mold sides are forced apart and flashing, or leakage of the molten thermoplastic material, occurs. A strain gauge sensor placed on the exterior of the mold surface adjacent to a parting line of a mold is able to sense the surface strain changes on the mold surface that occur over time as a result of the closing and opening forces. In response to surface strain changes, the strain gauge sensor emits an electrical signal, typically in the range of −10 to 10 Volts. The signal emitted by the strain gauge sensor is received and used by a controller to approximate one or more conditions within the mold, such as the pressure within the mold cavity or the location of the melt flow front. In certain molds in which the ratio of the length of the flow channel to the thickness of the molded part is great, i.e. molds having a high length-to-thickness (L/t) ratio, the pressure at the melt flow front may be approximated based on the signals emitted by the strain gauge sensor(s). These approximations may be useful for adjusting the injection molding process. For example, the amount of pressure within the mold cavity may be approximated and compared to a maximum permissible mold cavity pressure in an effort to ensure that the mold cavity is not damaged by excessive mold cavity pressure.

However, two key challenges make it difficult to approximate a condition within a mold cavity using an external sensor, such as a strain gauge, placed on a mold surface. First, not all areas of a mold surface experience a measurable condition, such as strain, in a way that accurately, reliably, and/or quantifiably corresponds with a condition within the mold, such as the pressure within the mold cavity or the location of the melt flow front, and therefore only some areas of a mold surface can be used to approximate one or more conditions within the mold, such as the pressure within the mold cavity or the location of the melt flow front. Injection molds come in a variety of shapes and sizes. Identifying areas of a mold surface that can be used to approximate a condition within the mold using an external strain gauge sensor has required testing a number of different areas on the mold surface, which can be time consuming, or making a blind guess that may turn out to be wrong. Second, even in areas on the surface mold that do experience a condition, such as strain, in a way that corresponds with a condition within the mold, external sensors often pick up some amount of "noise" generated during the molding process that does not correspond with a condition within the mold cavity. The noise measurements picked up by the external sensor must be distinguished from the meaningful measurements in order to accurately approximate one or more conditions within the mold. In some cases, the ratio of noise measurements to meaningful measurements is so high that conditions within the mold cannot be accurately approximated.

SUMMARY

Embodiments within the scope of the present disclosure are directed to external sensor kits that may be included in new injection molds or retrofitted into existing injection molds in order to approximate conditions within a mold, such as pressure or the location of a melt flow front. Strain gauge sensor kits are the type of external sensor primarily discussed, while other external sensor kits capable of detecting movement of mold halves as a proxy or tell-tale for internal conditions such as mold cavity pressure or flow front location, could achieve the same purpose as a strain gauge sensor and are within the scope of the present disclosure. For example, microwave sensor kits, x-ray sensor kits, ultrasonic sensor kits, air pressure sensor kits, air temperature sensor kits, sub-surface temperature sensor kits could all be substituted for the strain gauge sensors described and depicted below. Additionally, other types of external gauge sensor kits, such as electrical, electronic, mechanical, wireless, and fiber optic sensor kits, could be utilized instead of strain gauge sensor kits.

Because external sensor kit embodiments within the scope of the present disclosure are designed to be located and functional at a specific location in a mold, such embodiments eliminate the hunting and testing otherwise required to identify an area of a mold surface that experiences a condition, such as strain, in a way that corresponds with a condition within the mold. In addition, external sensor kit embodiments within the scope of the present disclosure are designed to amplify meaningful measurements obtained by the external sensor kit so that noise measurements do not prevent the approximation of conditions within a mold. Strain voltage measurements and other proxies for internal pressure or flow front position are often amplified prior to analytical evaluations, such as generating plots of pressure vs. time curve for a particular injection molding cycle. In most instances, strain measurements would still be amplified when taken with a strain gauge kit of the present disclosure, albeit the amount of amplification can be reduced, since the strain gauge kit disclosed herein serves to diminish the effects of noise. As such, by isolating and optimizing the efficacy of the strain gauge employing the apparatus and methods of the present disclosure, the strain gauge kit essentially serves to pre-amplify the strain gauge measurements. For example, strain gauge sensor kits may serve as a physical pre-amplifier for the meaningful strain measured in at least three ways. First, the strain gauge sensor may be placed on a coupon included in the kit, and the coupon may be made from a material having a flexural modulus that maximizes strain in the coupon. For example, brass and aluminum experience a greater strain than steel. Second, the coupon may have a geometry that maximizes strain at the location being sensed by the strain gauge sensor. Third, the strain gauge kit may include a hammer that exerts a force on the coupon when the injection mold is closed, and the force exerted by the hammer on the coupon (and thus the resulting strain in the coupon) may be maximized using the law of the lever. That is, the portion of the hammer that contacts or affects the coupon may be located some distance away from a fixed point, thus creating a lever arm that amplifies the strain within the coupon.

In some embodiments within the scope of the present disclosure, the external sensor kit includes a strain gauge sensor, a coupon, a support bracket, and a hammer. The strain gauge sensor is placed on a surface of the coupon and measures the strain in the coupon. The strain gauge sensors could be chosen from a variety of commercially available strain gauge sensors. For example, the Kistler "Surface Strain Sensor" Type 9232A of Kistler Group, Winterthur, Switzerland, or "Surface Mount Strain Gauges" Models SM-5A or SM-5B, available from Rocktest Telemac of Quebec, Canada, would work in embodiments within the scope of the present disclosure.

In some embodiments, the coupon is made from a material that has a flexural modulus that maximizes strain in the coupon, such as brass, aluminum, or a thermoplastic. In some embodiments, the coupon has a geometry that maximizes strain in the coupon. For example, in some embodiments, the coupon is brick-shaped with two cutouts configured to result in a cross-sectional area of the coupon near either end being larger than a cross-sectional area of the coupon near the center of the coupon. In some embodiments, the coupon is anvil-shaped and configured such that a cross-sectional area of the coupon near either end is larger than a cross-sectional area of the coupon near the center of the coupon.

In some embodiments, the coupon is secured within a support bracket adjacent to a parting line of a mold with at least one side of the coupon exposed along the parting side of the mold. The support bracket secures the coupon in a floating, non-restrictive matter. For example, the outer sides of the coupon may be loosely supported within a channel in the support bracket. A configuration of the support bracket that enables the coupon to float is important because anchoring the coupon to a portion of the support bracket may introduce mechanical forces that generate noise into the coupon, complicating the process of approximating a condition within the mold from the sensor reading of the coupon. To the extent that the coupon must be constrained, the coupon should be constrained so that the major axis of the strain is aligned with the sensing axis of the strain gauge. The sample can be pre-loaded with strain by, for example, using shim sheets placed between the sample and support bracket. A fine thread pitch or allowance in the mounting holes of the bracket could also be used to pre-load the sample. Structural finite-element analysis (FEA) tools can be used to determine how strain is distributed within the coupon and the major axis of the strain. One benefit of a strain gauge kit is that the FEA analysis can be done while the mold is being constructed prior to placement of the coupon. In contrast, in constructed molds upon which a strain gauge is placed directly, the FEA analysis must be done in multiple places to identify a proper location for a strain gauge, making the lengthy and expensive FEA analysis even more time-consuming and costly.

Combinations of the material, geometric, and support structure approaches to maximizing, or physically amplifying, strain in the coupon recited above are also within the scope of the present disclosure. Thus, one could select not only a particular material for the coupon that amplifies strain but also a particular strain-amplifying geometry, or a particular strain-amplifying material, a particular strain-amplifying geometry, and a particular strain-amplifying support structure. Alternately, one could select particular strain-amplifying geometry and strain-amplifying support structure, but not select a particularly-strain-amplifying material, or could select a strain-amplifying material and a strain-amplifying support structure, but not a particularly-strain-amplifying geometry.

When retrofitting an existing mold to include a strain gauge kit according to the present disclosure, the support bracket is essential in providing effective securement of a coupon. The support bracket may be secured to the existing mold using bolts or any other traditional securement mechanism or method. In new molds, a strain gauge kit would not necessarily need to be included because the mold could be initially manufactured to include a space along the parting line of the mold that could secure the coupon in a floating manner. A support bracket could be used in a new mold if so desired.

In some embodiments within the scope of the present disclosure, the hammer is secured adjacent to a parting line of a mold. The hammer is configured to contact or affect the coupon when the mold closes, and the force imparted by the hammer to the coupon creates the strain within the coupon that can be used to approximate conditions within the mold cavity. Ideally, the hammer is configured to maximize the force imparted to the coupon such that the coupon experiences greater force and resultant strain than it would if contacted directly by the opposite mold side in the absence of a hammer. To achieve this end, the hammer is designed so that the portion of the hammer that contacts or affects the coupon is located some distance away from the nearest fixed point securing the hammer. The distance between the fixed point and the portion of the hammer that contacts or affects the coupon acts as a lever arm, providing a mechanical advantage and amplifying the change in strain experienced by the coupon as a result of contact with the hammer. The hammer must be carefully designed, as the hammer can cause flashing to occur if the force exerted by the hammer on the coupon is enough to cause a gap between mold sides, allowing molten resin to leak out during the molding of parts. Given this potential problem with using a hammer, sufficient amplification of strain is preferably achieved through material selection and geometry of the coupon.

BRIEF DESCRIPTION OF THE DRAWINGS

While the specification concludes with claims particularly pointing out and distinctly claiming the subject matter that is regarded as the present disclosure, it is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF THE INVENTION

Figure 1:
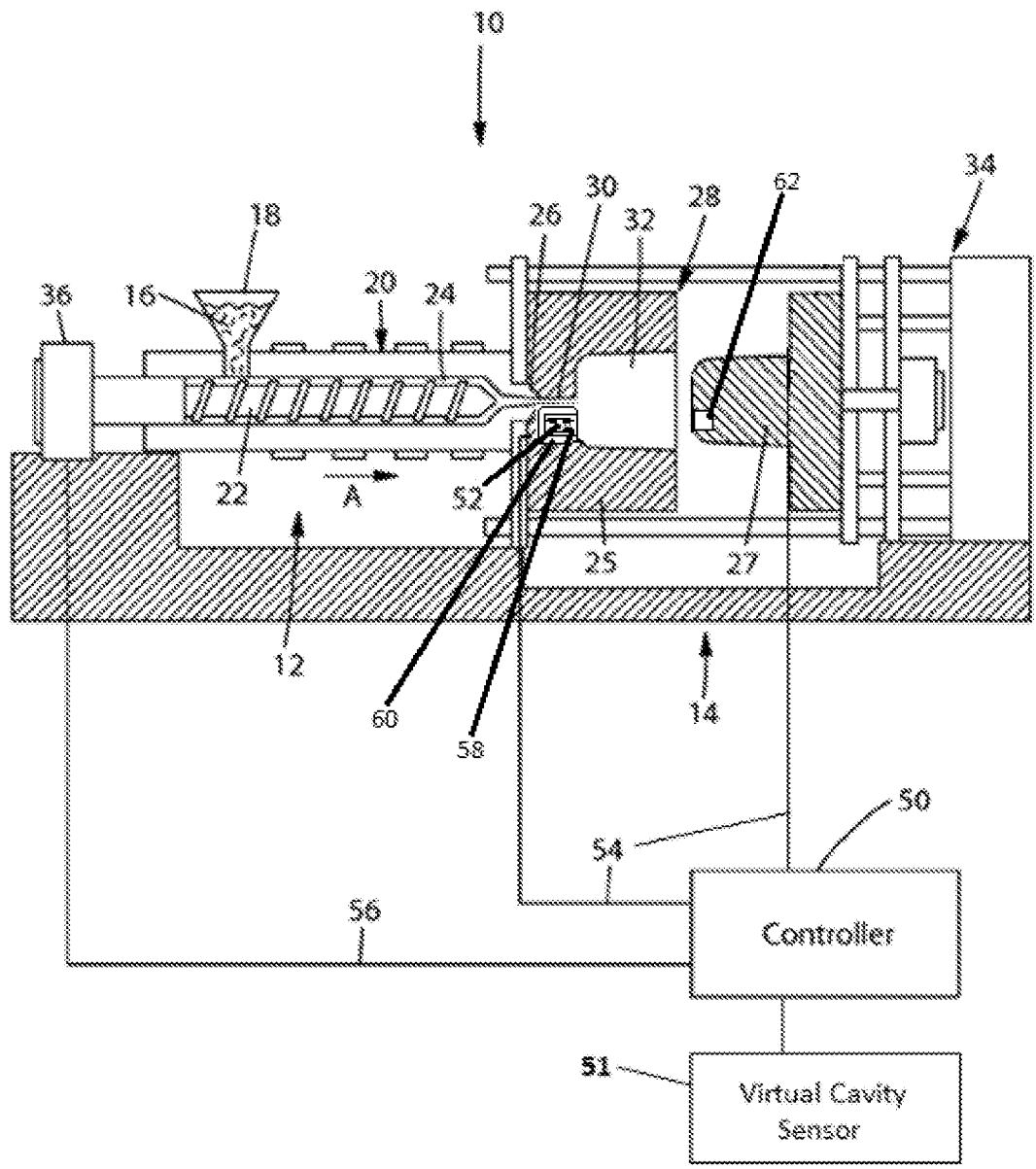
FIG. 1 illustrates, semi-schematically, an injection molding apparatus constructed according to the present disclosure, wherein a support bracket holds a coupon upon which a strain gauge sensor is placed adjacent to a first mold side in the vicinity of the nozzle to the mold cavity and a hammer is on a second mold side downstream of the nozzle and configured to contact the coupon when the mold is in a closed position.

Referring to the figures in detail, FIG. 1 illustrates an exemplary injection molding apparatus 10 for producing thermoplastic parts in high volumes (e.g., a class 101 injection mold, or an "ultra-high productivity mold", a class 102 (medium-to-high productivity mold), or class 103 (a medium productivity mold)). The injection molding apparatus 10 generally includes an injection system 12 and a clamping system 14. A thermoplastic material may be introduced to the injection system 12 in the form of thermoplastic pellets 16. The thermoplastic pellets 16 may be placed into a hopper 18, which feeds the thermoplastic pellets 16 into a heated barrel 20 of the injection system 12. The thermoplastic pellets 16, after being fed into the heated barrel 20, may be driven to the end of the heated barrel 20 by a ram, such as a reciprocating screw 22. The heating of the heated barrel 20 and the compression of the thermoplastic pellets 16 by the reciprocating screw 22 causes the thermoplastic pellets 16 to melt, forming a molten thermoplastic material 24. The molten thermoplastic material is typically processed at a temperature of about 130° C. to about 410° C.

The reciprocating screw 22 forces the molten thermoplastic material 24 toward a nozzle 26 to form a shot of thermoplastic material, which will be injected into a mold cavity 32 of a mold 28 via one or more gates. The molten thermoplastic material 24 may be injected through a gate 30, which directs the flow of the molten thermoplastic material 24 to the mold cavity 32. The mold cavity 32 is formed between first and second mold sides 25, 27 of the mold 28 and the first and second mold sides 25, 27 are held together under pressure by a press or clamping unit 34. The press or clamping unit 34 applies a clamping force during the molding process that is greater than the force exerted by the injection pressure acting to separate the two mold halves 25, 27, thereby holding the first and second mold sides 25, 27 together while the molten thermoplastic material 24 is injected into the mold cavity 32. In a typical high variable pressure injection molding machine, the press typically exerts 30,000 psi or more because the clamping force is directly related to injection pressure. To support these clamping forces, the clamping system 14 may include a mold frame and a mold base.

Once the shot of molten thermoplastic material 24 is injected into the mold cavity 32, the reciprocating screw 22 stops traveling forward. The molten thermoplastic material 24 takes the form of the mold cavity 32 and the molten thermoplastic material 24 cools inside the mold 28 until the thermoplastic material 24 solidifies. Once the thermoplastic material 24 has solidified, the press 34 releases the first and second mold sides 25, 27, the first and second mold sides 25, 27 are separated from one another, and the finished part may be ejected from the mold 28. The mold 28 may include a plurality of mold cavities 32 to increase overall production rates. The shapes of the cavities of the plurality of mold cavities may be identical, similar or different from each other. (The latter may be considered a family of mold cavities).

A controller 50 is communicatively connected with a strain gauge sensor 52 and a screw control 36. The strain gauge 52 is located on a coupon 58, which is secured to the exterior surface of a first mold side 25 near the parting line between the first mold side 25 and the second mold side 27 and in the vicinity of the nozzle 26 by a bracket 60. The controller 50 may include a microprocessor (or another suitable processing unit, or several such units), a non-transitory memory, and one or more communication links. In some embodiments, a hammer 62 is secured to the exterior surface of the second mold side 27 near the parting line between the first mold side 25 and the second mold side 27 and is configured to contact the coupon 58 when the mold 28 is closed. In other embodiments, a pushing portion of the hammer 62 may be secured to the exterior surface of the mold side 27 while a lever portion of the hammer 62 may be secured elsewhere within the injection molding apparatus 10 or may be integral with the coupon 54, with the hammer configured such that the pushing portion pushes the lever portion when the mold 28 is closed.

The strain gauge sensor 52 senses surface strain of the coupon 58. Data from the strain gauge sensor 52 may be communicated to a processor that calculates the change in the surface strain of the coupon 58. Electric signals 54 from the strain gauge sensor 52 may travel along one or more electrical paths, such as wires 54, depicted in FIG. 1 in solid lines, ranging in strength from −10 to 10 Volts. The controller 50 may be connected to the screw control 36 via wired connection 56. In other embodiments, the controller 50 may be connected to the screw control 36 via a wireless connection, a mechanical connection, a hydraulic connection, a pneumatic connection, or any other type of communication connection known to those having ordinary skill in the art that will allow the controller 50 to communicate with the screw control 36.

The controller 50 may use the change in surface strain calculated from the information provided by the strain gauge sensor 52 to approximate conditions, such as pressure or melt flow front position, within the mold cavity or, in certain molds, particularly in which the ratio of the length of the flow channel to the thickness of the molded part is large, at the melt flow front of the molten thermoplastic material 24. These approximations may then be used to adjust the injection molding process. For example, the amount of pressure within the mold cavity 32 may be approximated and compared to a maximum permissible mold cavity pressure in order to ensure that the mold cavity 32 is not damaged by excessive mold cavity pressure. If the amount of pressure within the mold cavity 32 is approximated to be dangerously close to the maximum permissible mold cavity pressure, or even in excess of a safety threshold well below the maximum permissible mold cavity pressure, the controller 50 may direct the screw control 36 to cease-injecting molten thermoplastic material. Other approximations may be used to control the molding process, such that variations in material viscosity, mold temperatures, melt temperatures, and other variations influencing filling rate, can be used to trigger adjustments to the injection molding system by the controller 50. These adjustments may be made immediately during the molding cycle, or corrections can be made in subsequent cycles. Furthermore, the approximations may be averaged over a number of cycles and then used to make adjustments to the molding process by the controller 50.

Additionally, the controller 50 is in communication with a virtual cavity sensor 51, which is implemented as a program, or a set of software instructions. More generally, however, a virtual cavity sensor can be implemented in hardware (e.g., as an application-specific integrated circuit (ASIC)), firmware, software, or any suitable combination thereof. In this disclosure, the term "virtual cavity sensor" can refer to a module that determines the value of a process variable, such as pressure, without directly measuring this process variable. The strain gauge sensor 52 and the virtual cavity sensor 51 together form a pressure controlling system that generates data relevant to strategic controlling of the pressure within the mold cavity 32. As used herein, the term "pressure controlling system" refers to any suitable group of components, which can include both software-implemented and hardware-implemented components, that generate a signal indicative of a condition within a mold cavity based on a signal indicative of another process variable.

For example, if based on the coupon surface strain information provided by the strain gauge sensor 52, a processor associated with the controller 50 determines that pressure within the mold cavity exceeds a trigger point (or is outside of a predetermined acceptable range), the virtual cavity sensor 51 signals the controller to adjust the screw control 36 to bring the pressure within the mold cavity back to a level below the trigger point (or within the predetermined acceptable range). As another example, if based on the coupon surface strain information provided by the strain gauge sensor 52, a processor associated with the controller 50 determines that the melt flow front has progressed beyond a trigger point (which may correlate to a percentage of the mold that has been filled), the virtual cavity sensor 51 signals the controller to adjust the screw control 36 to bring the pressure within the mold cavity to a predetermined acceptable finalizing pressure or range, which may involve a reduction in pressure to avoid over-packing a mold cavity, and thereby prevent unwanted flashing.

Figure 2:
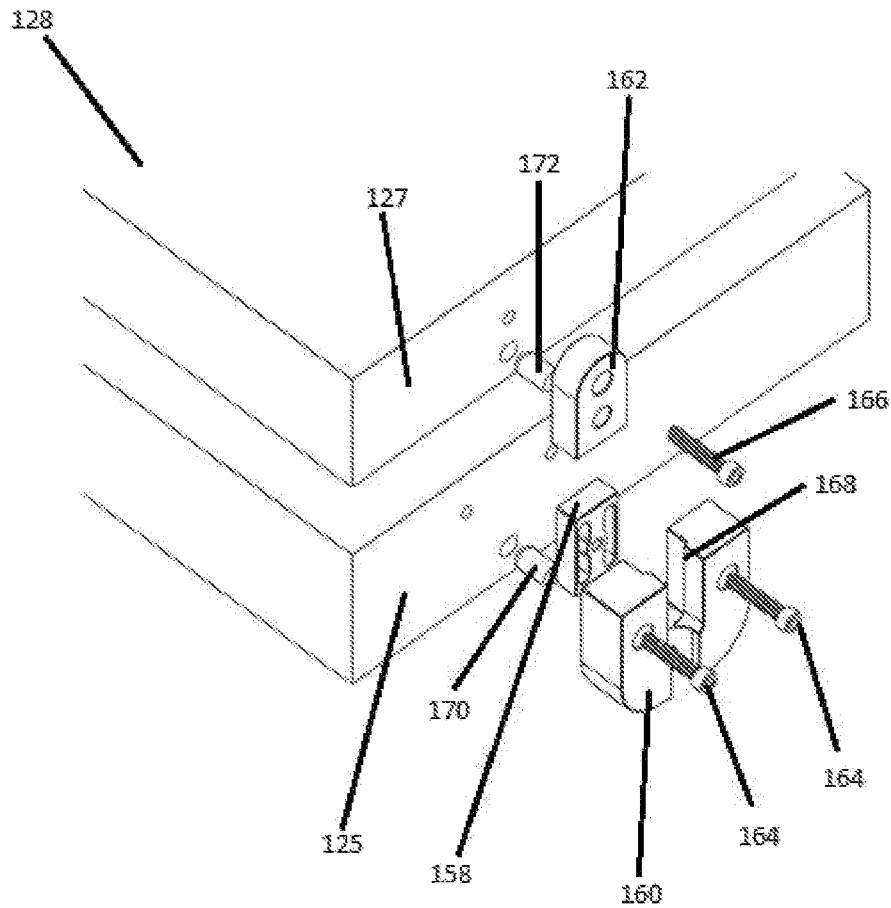
FIG. 2 illustrates an exploded perspective view a two mold sides of a mold, the first mold side having a support bracket securing a coupon in a floating manner and the second mold side having a hammer configured to contact the coupon when the mold is in a closed position.
Figure 3:
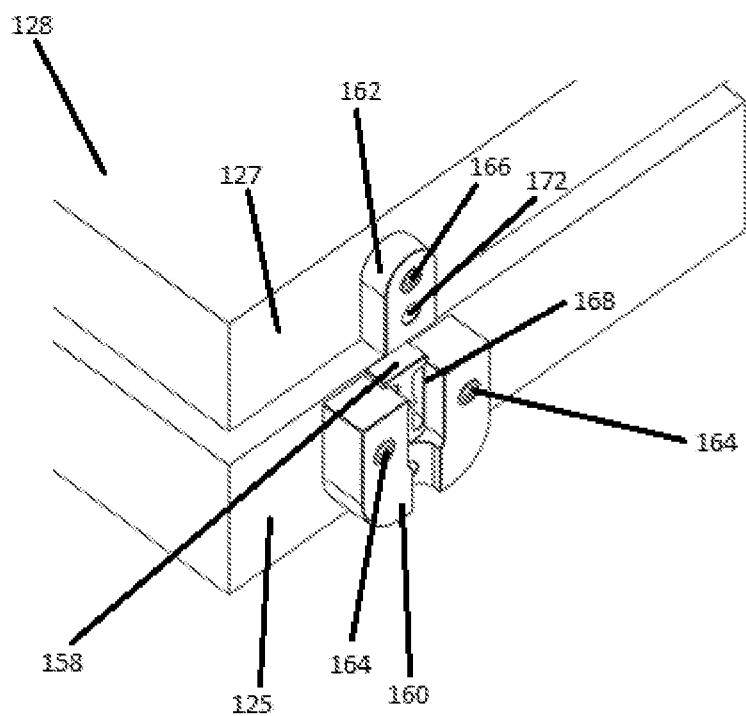
FIG. 3 illustrates a non-exploded perspective view of the embodiment depicted in FIG. 2.
Figure 4:
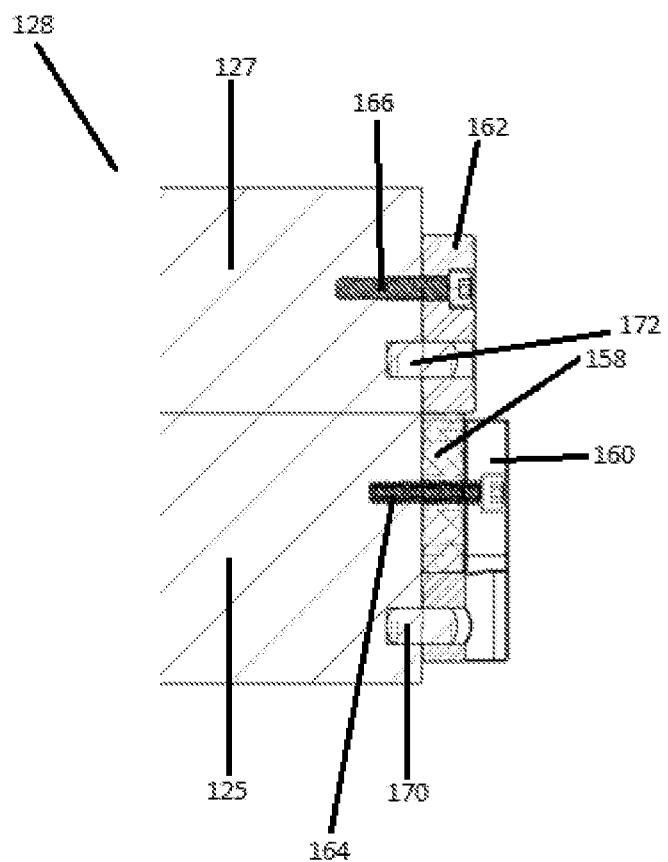
FIG. 4 illustrates a side view of the embodiment depicted in FIGS. 2 and 3.

FIG. 2 depicts the installation of a strain gauge kit comprising a strain gauge (not pictured), coupon 158, bracket 160, and hammer 162 into a mold 128. FIG. 3 depicts the strain gauge kit once it has been fully installed into the mold 128, and FIG. 4 provides a side view of the strain gauge kit installed into the mold 128. In FIGS. 2-4, a first mold side 125 has holes drilled into it, and the bracket 160 is secured to the first mold side 125 by bracket bolts 164 that are inserted through the bracket 160 into the first mold side 125 and by a bracket peg 170 which is inserted partially into the bracket 160 and partially into a hole in the first mold side 125. The bracket 160 has a bracket ledge 168 configured to secure a coupon 158 in a floating manner between the bracket 160 and an exterior side of the first mold side 125. The coupon 158 is not attached to the bracket 160 or the first mold side 125 because doing so might create strain within the coupon 158 that would interfere with the calculation of conditions within the mold cavity. One side of the coupon 158 is aligned with the parting line of the mold 128 along an edge of first mold side 125. A second mold side 127 has holes drilled into it, and the hammer 162 is secured to the second mold side 127 by a hammer bolt 166 that is inserted through the hammer 162 into the second mold side 127 and by a hammer peg 172 which is inserted partially into the hammer 162 and partially into a hold in the second mold side 127. A portion of the hammer 162 is aligned with the parting line of the mold 128 along an edge of second mold side 127 and is configured to contact the coupon 158 when the mold 128 is closed.

An existing injection molding apparatus may be retrofit to accommodate the strain gauge kit simply by drilling the holes necessary to mount the bracket 160 and hammer 162 and then installing the strain gauge kit. Alternately, new molds 128 may be designed to include such holes for mounting the bracket 160 and hammer 162 or the bracket 160 may be integral to the new mold. The number and location of holes, bracket bolts 164, bracket pegs 170, hammer bolts 166, and hammer pegs 172 may differ in various embodiments within the scope of the present disclosure.

Figure 5A:
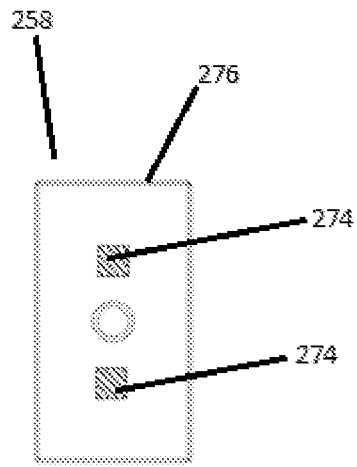
FIG. 5A illustrates a coupon for a strain gauge kit of the present disclosure.
Figure 5B:
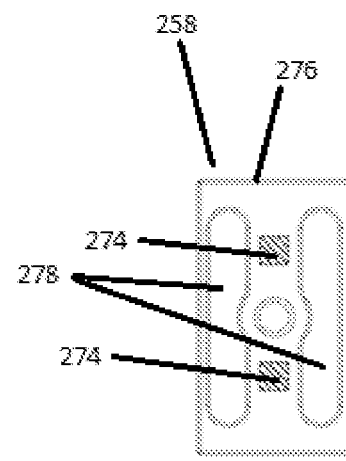
FIG. 5B illustrates a coupon for a strain gauge kit of the present disclosure having an arrangement of selected material compositions and a geometry that amplify the strain experienced by the coupon.
Figure 5C:
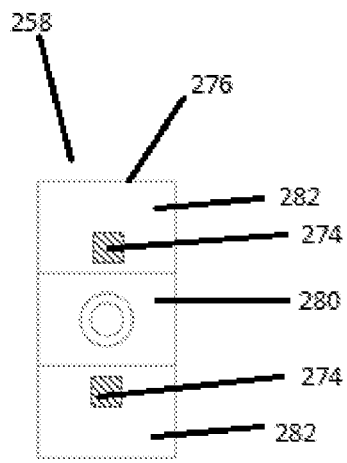
FIG. 5C illustrates a coupon for a strain gauge kit of the present disclosure having an arrangement of selected material compositions and a first alternate geometry that amplify the strain experienced by the coupon.
Figure 5D:
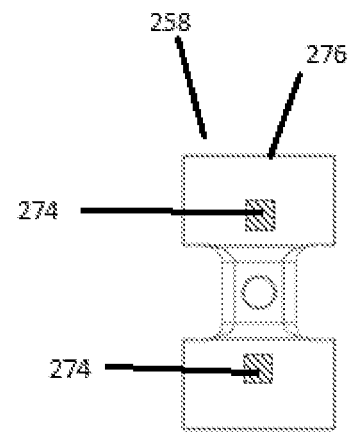
FIG. 5D illustrates a coupon for a strain gauge kit of the present disclosure having an arrangement of selected material compositions and a second alternate geometry that amplify the strain experienced by the coupon.

FIGS. 5A-5D depict various embodiments of coupons 258 within the scope of the present disclosure. The striped portions 274 of the coupons 258 indicate the locations where the ends of a strain gauge sensor would be placed. The coupon 258 in FIG. 5A is rectangular, and exposed side 276 is acted upon by a hammer or opposing mold side in order to create strain within the coupon 258, which is measured by a strain gauge and used to calculate conditions within a mold cavity. Each coupon 258 in FIGS. 5B-5D is configured to amplify the strain it experiences when a mold is closed relative to the strain that would be experienced if the coupon 258 had the configuration depicted in FIG. 5A. For example, FIGS. 5B and 5D depict coupons 258 with geometries in which the cross-sectional area of the coupon 258 in a direction perpendicular to the direction the hammer acts upon exposed side 276 decreases toward the center of the coupon 258. As a result, the center of the coupon 258 experiences greater strain, which can more easily be measured by a strain gauge. In FIG. 5B, this reduction in cross-sectional area is accomplished by openings 278 in the center of the coupon 258, which otherwise has a rectangular shape. In FIG. 5D, the reduction in cross-sectional area is accomplished by having a coupon 258 with an anvil-like shape. In FIG. 5C, the amplification of strain is achieved by making the coupon 258 from two different materials. Specifically, a center portion 280 is made from a material having a low flexural modulus while outer portions 282 are made from a material having a higher flexural modulus.

Figure 6:
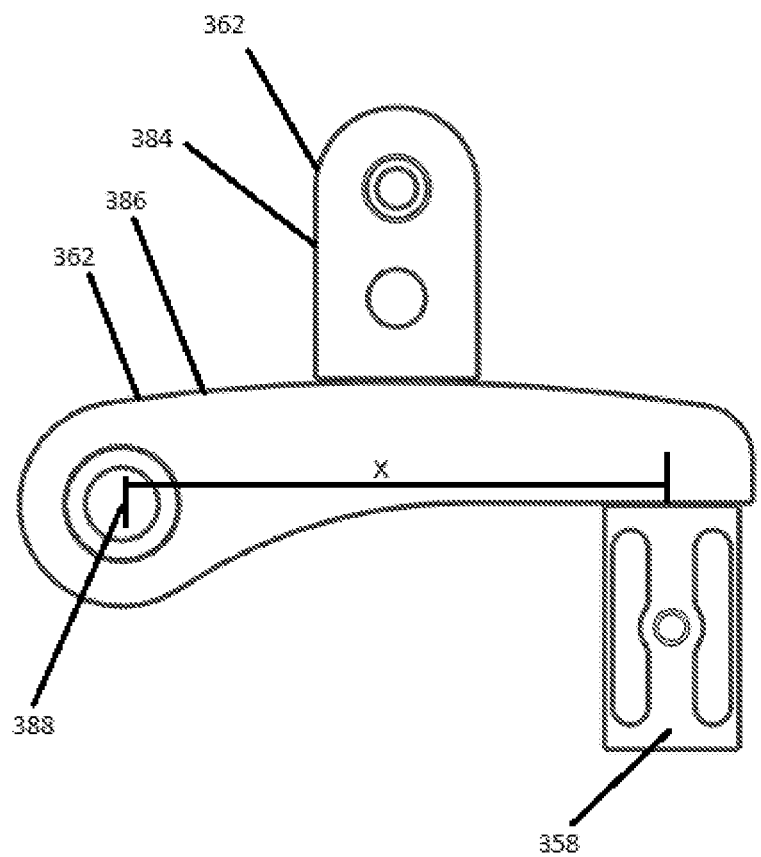
FIG. 6 illustrates a hammer having a pushing portion of the hammer attached to one mold side and a lever portion of the hammer attached to the other mold side wherein the lever portion is configured to be pushed by the pushing portion into a coupon, thereby maximizing the force exerted on the coupon and the resultant strain within the coupon.

FIG. 6 illustrates a hammer 362 having a pushing portion 384 that is connected to one mold side and a lever portion 386 that is connected at a pivot 388 to the other mold side. The pushing portion 384 pushes on the lever portion 386, which then exerts that force on the coupon 358. Because the force imparted by the pushing portion 384 on the lever portion 386 acts over the distance X between the pivot 388 and the coupon 358, the force is amplified pursuant to the law of the lever when it hits the coupon 358. As a result, the strain experienced by the coupon 358 is amplified and easier to use to approximate conditions within a mold.

Figure 7:
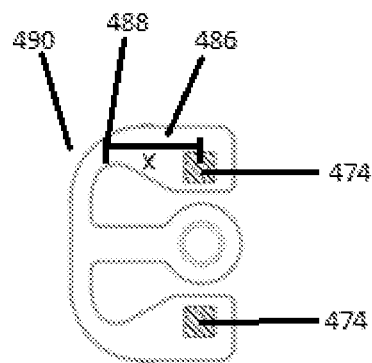
FIG. 7 illustrates an E-shaped hammer that is integral with a coupon for a strain gauge kit of the present disclosure.
Figure 8:
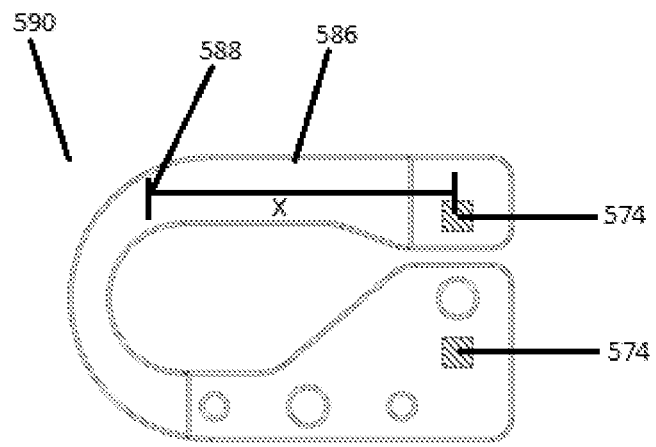
FIG. 8 illustrates a C-shaped hammer that is integral with a coupon for a strain gauge kit of the present disclosure.

FIGS. 7 and 8 depict combined coupon/hammers 490 and 590 respectively. Coupon/hammer 490 has an E-configuration, while coupon/hammer 590 has a C-configuration. The striped portions 474 and 574 indicate where a strain gauge would be located. A separate pushing portion 484, 584 (not depicted) acts on the lever portion 486, 586 of each respective combined coupon/hammer 490, 590. Because the force imparted by the pushing portion 484 or 584 (not depicted) on the lever portions 486 or 586 acts over distance X between the pivot area 488 or 588 and the portion of the coupon/hammer 490 or 590 on which the strain gauge is located, the force is amplified pursuant to the law of the lever within each coupon/hammer 490 or 590, making it easier to approximate conditions within a mold.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be appreciated to those skilled in the art that various other changes and modifications can be made without departing from the spirit and scope of the invention. It is therefore intended to cover in the appended claims all such changes and modifications that are within the scope of this invention.

What is claimed is:

1. An external sensor kit for an injection molding system comprising:
   a bracket attachable to a first mold side of the injection molding system;
   a coupon securable between the first mold side and the bracket;
   a hammer attachable to a second mold side across from the coupon; and
   an external sensor disposed on the coupon,
   wherein the hammer comprises a pushing portion and a lever portion, and the pushing portion is attachable to the second mold side, and the lever portion comprises a pivot located some distance away from the external sensor.

2. The external sensor kit of claim 1, wherein the external sensor is a strain gauge sensor.

3. The external sensor kit of claim 1 wherein the lever portion of the hammer is separate from the pushing portion of the hammer.

4. The external sensor kit of claim 3, wherein the lever portion is attachable to the first mold side.

5. The external sensor kit of claim 4, wherein the lever portion of the hammer is integral with the coupon.

6. The external sensor kit of claim 5, wherein the integral hammer and coupon form one of a C-configuration and an E-configuration.

7. An external sensor kit for an injection molding system comprising:
   a bracket attachable to a first mold side of the injection molding system;
   a coupon securable between the first mold side and the bracket;
   a hammer attachable to a second mold side across from the coupon; and
   an external sensor disposed on the coupon,
   wherein the coupon is configured to maximize the strain experienced by the coupon when the hammer imparts the force to the coupon; and
   wherein the coupon comprises a first material and a second material have a lower flexural modulus than the first material, and the arrangement of the first material and the second material within the coupon maximizes the strain experienced by the coupon.

8. The external sensor kit of claim 7, wherein the geometry of the coupon maximizes the strain experienced by the coupon when the hammer imparts the force to the coupon.

9. The external sensor kit of claim 7, wherein the external sensor is a strain gauge sensor.

* * * * *

UNITED STATES PATENT AND TRADEMARK OFFICE
CERTIFICATE OF CORRECTION

| | | |
|---|---|---|
| PATENT NO. | : 10,399,264 B2 | Page 1 of 1 |
| APPLICATION NO. | : 15/448992 | |
| DATED | : September 3, 2019 | |
| INVENTOR(S) | : Chow-Chi Huang et al. | |

It is certified that error appears in the above-identified patent and that said Letters Patent is hereby corrected as shown below:

In the Claims

At Column 12, Line 16, "have a" should be -- having a --.

Signed and Sealed this
Seventh Day of April, 2020

Andrei Iancu
*Director of the United States Patent and Trademark Office*